[19] United States Patent
Köppe et al.

[11] 4,438,143
[45] Mar. 20, 1984

[54] 1-ARYLOXY-3-ALKYLAMINO-2-PROPANOLS AND PHARMACEUTICAL COMPOSITIONS CONTAINING THEM

[75] Inventors: Herbert Köppe; Werner Kummer; Helmut Stähle; Gojko Muacevic, all of Ingelheim; Werner Traunecker, Münster-Sarmsheim, all of Fed. Rep. of Germany

[73] Assignee: Boehringer Ingelheim KG, Ingelheim am Rhein, Fed. Rep. of Germany

[21] Appl. No.: 420,796

[22] Filed: Sep. 21, 1982

Related U.S. Application Data

[63] Continuation-in-part of Ser. No. 383,624, Jun. 1, 1982, abandoned, which is a continuation of Ser. No. 254,510, Apr. 15, 1981, abandoned.

[30] Foreign Application Priority Data

Apr. 25, 1980 [DE] Fed. Rep. of Germany ....... 3015991

[51] Int. Cl.³ .................. A61K 31/275; C07C 121/80
[52] U.S. Cl. ............................... 424/304; 260/465 D
[58] Field of Search .................... 260/465 D; 424/304

[56] References Cited

U.S. PATENT DOCUMENTS 3,712,927 1/1973 Howe et al. ............... 260/465 E X

FOREIGN PATENT DOCUMENTS 2503222 7/1976 Fed. Rep. of Germany.

Primary Examiner—Dolph H. Torrence

Attorney, Agent, or Firm—Hammond & Littell, Weissenberger & Dippert

[57] ABSTRACT

This invention relates to compounds of the formula

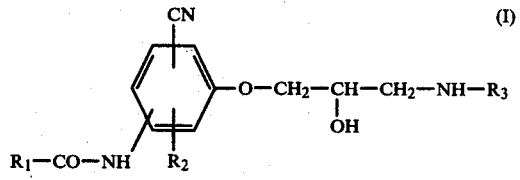

wherein
$R_1$ represents a linear or branched alkyl of from 1 to 20 carbon atoms;
$R_2$ represents a hydrogen or halogen atom, a linear or branched alkyl or alkoxy of from 1 to 4 carbon atoms, or a divalent group $-CH=CH-CH=CH-$ or $-(CH_2)_n-$, in which n is an integer of from 3 to 5, with the free valences bonded in the o-position relative to one another; and
$R_3$ represents a linear or branched alkyl of from 3 to 10 carbon atoms, with the provisos that $R_3$ is not tert.butyl when $R_1$ is ethyl or propyl and $R_2$ is a hydrogen atom and that $R_3$ is not isopropyl when $R_1$ is propyl and $R_2$ is a hydrogen atom, or a non-toxic, pharmacologically acceptable acid addition salt thereof. The compounds of Formula I are useful for treatment and prophylaxis of diseases of the coronaries, for the treatment of hypertension, and for treatment of cardiac arrhythmia, particularly tachycardia.

9 Claims, No Drawings

1-ARYLOXY-3-ALKYLAMINO-2-PROPANOLS AND PHARMACEUTICAL COMPOSITIONS CONTAINING THEM

CROSS-REFERENCE TO RELATED APPLICATIONS

This application is a continuation-in-part of U.S. patent application Ser. No. 383,624, filed June 1, 1982, abandoned, incorporated herein by reference, which in turn is a continuation of U.S. patent application Ser. No. 254,510, filed Apr. 15, 1981, now abandoned.

FIELD OF THE INVENTION

This invention relates to novel 1-aryloxy-3-alkylamino-2-propanols. More particularly, this invention relates to said 1-aryloxy-3-alkylamino-2-propanols and non-toxic, pharmacologically acceptable acid addition salts thereof, the preparation of said compounds, and their use in pharmaceutical compositions.

DETAILED DESCRIPTION OF THE INVENTION

Applicants' invention is directed to compounds of the formula

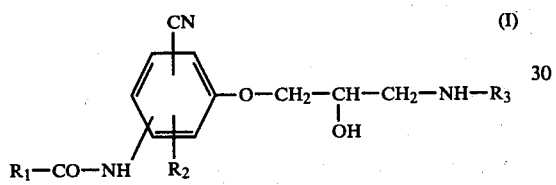

wherein $R_1$ represents a linear or branched alkyl of from 1 to 20 carbon atoms;

$R_2$ represents a hydrogen or halogen atom, a linear or branched alkyl or alkoxy of from 1 to 4 carbon atoms, or a divalent group $-CH=CH-CH=CH-$ or $-(CH_2)_n-$, in which n is an integer of from 3 to 5, with the free valences bonded in the o-position relative to one another; and $R_3$ represents a linear or branched alkyl of from 3 to 10 carbon atoms, with the provisos that $R_3$ is not tert.-butyl when $R_1$ is ethyl or propyl and $R_2$ is a hydrogen atom and that $R_3$ is not isopropyl when $R_1$ is propyl and $R_2$ is a hydrogen atom, and the non-toxic, pharmacologically acceptable acid addition salts thereof. The invention is also directed to the preparation of said compounds and the use thereof in pharmaceutical compositions.

In a preferred embodiment of the compounds of Formula I, $R_1$ represents a linear or branched alkyl of from 1 to 7 carbon atoms, particularly an n-pentyl;

$R_2$ represents a hydrogen atom; and $R_2$ represents an alkyl branched in the vicinity of the amino group, that is, in the α- or β-position of the alkyl, particularly an isopropyl or tert.butyl, with the provisos that $R_3$ is not tert.butyl when $R_1$ is ethyl or propyl and that $R_3$ is not isopropyl when $R_1$ is propyl.

The compounds of Formula I may be prepared by the following methods:

Method A

A compound of the formula

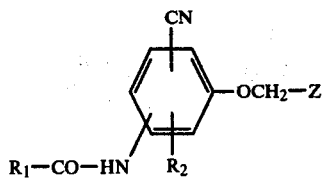

wherein $R_1$ and $R_2$ are as defined above and Z represents the group

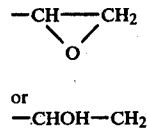

or $-CHOH-CH_2-Hal$ in which Hal represents a halogen atom, is reacted with an amine of the formula $NH_2-R_3$      (III)

wherein $R_3$ is as defined above.

Method B

An oxazolidine derivative of the formula

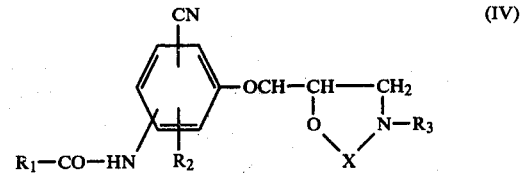

wherein $R_1$, $R_2$, and $R_3$ are as defined above, and X represents a $-CO-$ or $-CH_2-$ group or the group

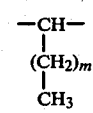

wherein m is an integer of from 0 to 5, is hydrolyzed with sodium or potassium solution in water or in a mixture of alcohol, such as methanol, and water.

Method C

A compound of the formula

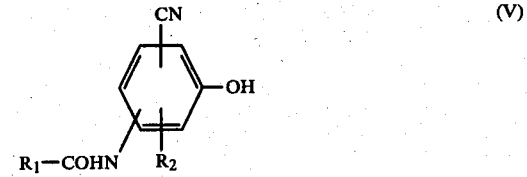

wherein $R_1$ and $R_2$ are as defined above, or a salt of the phenol of Formula V, is reacted with an azetidinol derivative of the formula

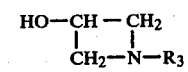

wherein R₃ is as defined above, in an anhydrous medium.

The oxazolidinones of Formula IV, that is, the compounds where X is —CO—, may be prepared, for example, by reacting an epoxide of Formula II with a urethane of the formula

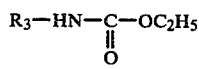 (VII)

wherein R₃ is as defined above. The compounds of Formula VII may be prepared from ethyl chloroformate and an amine of Formula III.

The starting phenols of Formula V and the azetidinols of Formula VI may be prepared according to methods known from the literature [cf., for example, Chem. Pharm. Bull. (Japan), Vol. 22 (7), 1974, page 1490].

The compounds according to the invention have an asymmetric carbon atom in the —(CH)OH— group and therefore occur both as racemates and in the form of optical antipodes. These may be isolated not only by separation of the racemates with conventional auxiliary acids, such as dibenzoyl-D-tartaric acid, di-p-toluyl-D-tartaric acid, or D-3-bromo-caphor-8-sulfonic acid, but also by use of the corresponding optically active starting material.

The compounds of Formula I are basic and therefore form addition salts with inorganic or organic acids. Examples of non-toxic, pharmacologically acceptable acid addition salts are those formed with hydrochloric acid, hydrobromic acid, sulfuric acid, methane-sulfonic acid, maleic acid, acetic acid, oxalic acid, lactic acid, tartaric acid, 8-chlorotheophylline, or the like.

The compounds of the present invention, that is, those embraced by Formula I above and their non-toxic, pharmacologically acceptable acid addition salts, have useful pharmaco-dynamic properties. More particularly, in the animal test on guinea pigs they exhibit β-adrenolytic properties and may therefore be used in human medicine, for example, for treatment and prophylaxis of diseases of the coronaries, particularly angina pectoria, and for treatment of cardiac arrhythmia, particularly tachycardia.

The hypotensive properties of the compounds are also of therapeutic interest, as are the metabolic properties. In comparison with known β-receptor blockers, for example, the commercial product of similar structure 1-(2-acetyl-4-butyroylaminophenoxy)-2-hydroxy-3-isopropyl-aminopropane (Acebutolol), the compounds have the advantage of a considerably lower toxicity, enhanced β-isoprenaline antagonistic activity and excellent organ selectivity. These parameters were measured by means of the following test methods:

1. Inhibition of the isoprenaline tachycardia (isoprenaline antagonistic activity)

Method: Inhibition of the tachycardiac reaction to a standard dose of isoprenaline and effect upon the basal heart rate of increasing i.v. dosages of a β-adrenolytic.

Animal material: Guinea pigs of both sexes with body weights of 270 to 350 gm, group keeping; standard feed and water until beginning of test ad libitum; and withdrawal of nutrition sixteen hours before beginning of test.

Anesthesia: Ethylurethane 1.75 gm/kg as a 20% solution intraperitoneally; if required, it was reinjected.

Preparation: Cannulation of a Vena jugularis exterior for intravenous injection: Insertion of a tracheal cannula and artificial respiration; subcutaneous needle electrodes for recording of the ECG, as a rule, extremity lead II, recording rate 24 mm/sec; and rectal thermometer for control of body temperature which is kept constant at 34° to 36° C. by means of an infrared heat lamp controlled by an automatic electronic heat sensing device.

Test Procedure: The heart rate is determined by counting the r-waves in the ECG, each from a recording time of 3 to 4 seconds. About 30 minutes after the preparation the normal heart rate is recorded an average of five times in intervals of 2 minutes. Subsequently, 1 μg/kg of isoprenaline is injected i.v. as adrenergic stimulant, and afterwards the heart rate is recorded repeatedly for 30 seconds every 3 minutes. The injections of isoprenaline are repeated during the whole time of the test at intervals of 30 minutes. If the spontaneous rate remains almost constant and if the tachycardiac reaction upon the first 2 to 3 isoprenaline administrations is homogeneous, then the first dose of the test compound is injected i.v.—15 minutes after the last and 15 minutes before the next isoprenaline reaction. Further doses of the test compound increasing in geometric series follow at intervals of 60 minutes until a distinct inhibition of the isoprenaline tachycardia has been reached.

2. Test for cardioselectivity on the conscious guinea pig

Principle: According to the method of D. Dunlop and R. G. Shanks [Brit. J. Pharmacol. 32, 201 (1968)], conscious guinea pigs are exposed to a lethal dose of a histamine aerosol. By pre-treatment with isoprenaline the animals are protected from the lethal effect of the histamine. A β-adrenolytic neutralizes the isoprenaline, so that the protection against histamine bronchospasms is lost if a non-cardioselective substance is involved. If a cardiac-active β-adrenolytic substance does not show any antagonism against isoprenaline in this test, the presence of cardio-selectivity (for so-called β₁-receptors) may be assumed.

Animal material: Guinea pigs of both sexes (6 animals per dose), with 350 to 440 gm body weight, group keeping; standard feed and water until beginning of test ad libitum; and withdrawal of feed sixteen hours before beginning of test.

Test Procedure: Groups of 6 animals each (3 male and 3 female) are treated subcutaneously with 5 or more different doses of the β-adrenolytic. Fifteen minutes later they get a contralateral subcutaneous injection of 0.01 mg/kg isoprenaline. After another 15 minutes have passed, the animals are placed into a cylindrical chamber of 2 liters capacity and are exposed for 45 seconds to an aqueous histamine aerosol (1.25%), and subsequently the mortality is evaluated.

Evaluation: The mortality is plotted against the logarithm of the dose, and the LD₅₀ is determined according to J. LITCHFIELD and F. WILCOXON (J. Pharmacol. Exp. Therap. 96, 99–113, 1949). With the LD₅₀ from this test and the cardiac ED₅₀ from the isoprenaline tachycardia inhibition test (anesthetized guinea pigs), a selectivity quotient (LD₅₀/ED₅₀) is formed. A substance is considered to be cardioselective if the quotient is larger than 1.

Particularly effective are those compounds of Formula I wherein $R_3$ represents an isopropyl or tert.butyl group, that is, substituted p-acylamino-1-phenoxy-3-alkylamino-2-propanols. Especially effective are 1-(2-cyano-4-n-hexanoylamino-phenoxy)-3-tert.butylamino-2-propanol and 1-(2-cyano-4-n-hexanoylamino-phenoxy)-3-isopropylamino-2-propanol and the acid addition salts thereof.

Compounds somewhat structurally related to those set forth herein are disclosed in Howe et al., U.S. Pat. No. 3,712,927 and German published application (DE-OS) No. 25 03 222. To demonstrate the superiority of the compounds of Formula I, the closest compound of the Howe et al. patent, i.e., the compound of Example 9; the compounds represented at page 12, lines 22 and 23, of page 12 of DE-OS No. 25 03 222; and compounds according to the invention were tested with regard to β-adrenolytic activity, i.e., isoprenaline antagonistic activity, and cardioselectivity. The testing was conducted according to test methods 1 and 2 described above, and the results were as follows:

TABLE

| Compound | Isoprenaline Antagonism Effect (DCI = 1) | Selectivity (SQ) |
|---|---|---|
| 1-(2-Cyano-4-propionamido-phenoxy)-3-tert.-butylamino-2-propanol oxalate hemihydrate (Howe et al. patent, Example 9)* | 23 | >24 |
| 1-(2-Cyano-4-n-butyroylamino-phenoxy)-3-isopropylamino-2-propanol (DE-OS No. 25 03 222)* | 4.8 | 8 |
| 1-(2-Cyano-4-n-butyroylamino-phenoxy)-3-tert. butylamino-2-propanol (DE-OS No. 25 03 222)* | 37 | 0 |
| 1-(2-Cyano-4-n-hexanoylamino-phenoxy)-3-isopropylamino-2-propanol (Example 1 herein) | 78 | 96 |
| 1-(2-Cyano-4-n-acetylamino-phenoxy)-3-tert.-butylamino-2-propanol (Example 2 herein) | 56 | — |
| 1-(2-Cyano-4-n-hexanoylamino-phenoxy)-3-tert. butylamino-2-propanol hydrochloride (Example 3 herein) | 140 | >96 |
| 1-(2-Cyano-4-n-octanoylamino-phenoxy)-3-isopropylamino-2-propanol (Example 23 herein) | 39 | 67 |

*Comparison

As can be seen from the table above, the compounds according to the invention unexpectedly demonstrate enhanced isoprenaline antagonistic activity and selectivity as compared to the compounds disclosed by Howe et al. and DE-OS No. 25 03 222.

The active substances according to the invention may be used to prepare the conventional galenic forms, such as tablets, coated tablets, solutions, emulsions, powders, capsules or sustained release forms, using the conventional pharmaceutical excipients and the usual methods of production. Corresponding tablets may be produced, for example, by mixing the active substances with known excipients, for example, inert diluents such as calcium carbonate, calcium phosphate, or lactose, disintegrants such as corn starch or alginic acid, binders such as starch or gelatine, lubricants such as magnesium stearate or talc, and/or agents for obtaining sustained release, such as carboxypolymethylene, carboxymethylcellulose, cellulose acetate phthalate, or polyvinyl acetate.

The tablets may consist of several layers. Coated tablets may be produced analogously by coating cores produced in the same way as the tablets with the agents conventionally used for coating tablets, for example, collidone or shellac, gum arabic, talc, titanium dioxide, or sugar. To obtain sustained release or to avoid incompatibilities, the core may also consist of several layers. Similarly, the coating of the tablet may consist of several layers to obtain sustained release, for which the excipients mentioned above with reference to the tablets may be used.

Syrups of the active substances or combinations of active substances according to the invention may additionally contain a sweetener, such as saccharin, cyclamate, glycerin, or sugar, and a flavor-improving agent, for example, a flavoring such as vanillin or orange extract. They may also contain suspension agents or thickeners, such as sodium carboxymethylcellulose, wetting agents, for example, condensation products of fatty alcohols with ethylene oxide, or preservatives such as p-hydroxybenzoates.

Injection solutions are prepared in the usual way, for example, by adding preservatives such as p-hydroxybenzoates or stabilizers such as complexones, and these are decanted into injection vials or ampules.

Capsules containing the active substances or combinations of active substances may be prepared, for example, by mixing the active substances with inert carriers such as lactose or sorbitol and then filling gelative capsules with the mixture.

Suitable suppositories may be prepared, for example, by mixing the active ingredients or combinations of active ingredients intended therefor, with conventional carriers such as neutral fats or polyethyleneglycol or derivatives thereof.

The compounds according to the invention are also suitable for combining with other pharmacodynamically active substances such as, for example, coronary dilators, sympathicomimetics, cardiac glycosides, and tranquillizers.

One effective oral dosage unit of the compounds according to the present invention is from about 1 to 300 mg (from about 0.013 to 4.0 mg/kg body weight), preferably from about 5 to 100 mg (from about 0.07 to 1.33 mg/kg body weight). The parental dosage unit range is from about 1 to 20 mg (from about 0.013 to 0.26 mg/kg body weight).

The following examples illustrate the present invention and will enable others skilled in the art to understand it more completely. It should be understood, however, that the invention is not limited solely to the particular examples given below.

EXAMPLES

The preparation of compounds of the invention is described in the examples below.

EXAMPLE 1

1-(2-Cyano-4-n-hexanoylamino-phenoxy)-3-isopropylamino-2-propanol

Ten grams (0.035 mol) of 1-(2-cyano-4-hexanoylamino-phenoxy)-2,3-epoxypropane were dissolved in 100 ml of ethanol and, after the addition of 8.3 gm (0.14 mol) of isopropylamine, the mixture was refluxed for one hour. The solvent was evaporated in vacuo, and the remaining residue solidified. It was recrystallized twice from acetonitrile. The white crystalline base was recovered by suction filtration and dried.

Yield: 3.8 gm; M.p.: 115°–117° C.

EXAMPLE 2

1-(2-Cyano-4-n-acetylamino-phenoxy)-3-tert.butylamino-2-propanol

Eleven grams of 1-(2-cyano-4-acetylamino-phenoxy)-2,3-epoxypropane were refluxed for ninety minutes with 10 ml of tert.butylamine in 80 ml of ethanol. The solvent was distilled off in vacuo, the residue was digested with $H_2O$ and acidified with HCl, and the neutral substances were extracted with ethyl acetate. The aqueous phase was made alkaline with NaOH, and the amine obtained was taken up in ethyl acetate. After the organic phase was washed with $H_2O$ and dried over $MgSO_4$, the solvent was distilled off in vacuo. The residue was recrystallized from acetonitrile.

Yield: 5.9 gm; M.p.: 122°–123° C.; TLC: uniform.

EXAMPLE 3

1-(2-Cyano-4-n-hexanoylamino-phenoxy)-3-tert.butylamino-2-propanol hydrochloride Ten grams (0.03 mol) of 1-(2-cyano-4-hexanoylamino-phenoxy)-2,3-epoxypropane were dissolved in 100 ml of ethanol and then mixed with 7.3 gm (0.1 mol) of tert.butylamine and refluxed for one hour. After cooling, the solvent was distilled off in vacuo, and the residue was purified over a silica gel column [mixture of solvents: ethyl acetate/isopropanol/$NH_4OH$ (14:6:1)]. The uniform fractions were combined, washed with dilute NaOH and $H_2O$, and dried, and then the drying agent was removed by suction filtration. The mixture of solvents was evaporated, and the residue was dissolved in ether and acidified with alcoholic HCl. The crystals that precipitated were recovered by filtration. The product was recrystallized from acetonitrile, with the addition of ether. Yield: 4.6 gm. The pure white hydrochloride melted at 143°–145° C.

The compounds set forth in Examples 4 and 5 were prepared using procedures analogous to that of Example 3.

EXAMPLE 4

1-(2-Cyano-4-n-octanoylamino-phenoxy)-3-tert.-butylamino-2-propanol hydrochloride From 10 gm (0.03 mol) of 1-(2-cyano-4-octanoylamino-phenoxy)-2,3-epoxypropane and 7.3 gm (0.1 mol) of tert.butylamine, 2.8 gm of clean base were obtained, and this was converted to the above-mentioned hydrochloride. M.p. 155°–157° C.

EXAMPLE 5

1-[2-Cyano-4-(3,3-dimethylbutyroyl)-amino-phenoxy]-3-isobutylamino-2-propanol hydrochloride After aminolysis of 7.5 gm (0.026 mol) of 1-[2-cyano-4-(3,3-dimethylbutyroyl)-phenoxy]-2,3-epoxypropane with 7.3 gm (0.1 mol) of isobutylamine, working up, and precipitated as the hydrochloride, 1.6 gm of the salt were obtained. M.p.: 163°–166° C.

EXAMPLE 6

1-[2-Cyano-4-(2-ethylhexanoyl)-amino-phenoxy]-3-isopropylamino-2-propanol hydrochloride Fifteen grams (0.043 mol) of 1-[2-cyano-4-(2-ethylhexanoyl)-amino-phenoxy]-3-chloro-2-propanol were dissolved in 80 ml of ethanol, 14.4 ml (0.17 mol) of isopropylamine were added, and the mixture was refluxed for two hours. The solvent was then distilled off, and the residue was purified on a silica gel column [mixture of eluants: ethyl acetate/isopropanol/$NH_4OH$ (14:6:1)]. The pure base obtained was recrystallized from ethyl acetate with the addition of petroleum ether. The crystals were dissolved in acetonitrile and acidified with alcoholic hydrochloric acid, and crystallization was initiated by the addition of ether. The crystals were pure white. Yield: 2.9 gm. M.p: 169°–170° C.

The compounds mentioned in Examples 7 to 15 were prepared using procedures analogous to that of Example 6.

EXAMPLE 7

1-(2-Cyano-6-n-hexanoylamino-phenoxy)-3-isopropylamino-2-propanol hydrochloride

From 12.9 gm (0.04 mol) of 1-(2-cyano-6-hexanoylamino-phenoxy)-3-chloro-2-propanol and 13.6 ml (0.16 mol) of isopropylamine, 5.3 gm of amino-alcohol were obtained, which were converted into the hydrochloride by the addition of HCl. Yield: 4.7 gm; M.p.: 107° C.

EXAMPLE 8

1-(2-Cyano-6-n-pentanoylamino-phenoxy)-3-isopropylamino-2-propanol hydrochloride From 11 gm (0.036 mol) of corresponding chlorohydrin and 9.4 ml (0.11 mol) of isopropylamine, 2.9 gm of hydrochloride were obtained after the addition of HCl. M.p.: 105°–107° C.

EXAMPLE 9

1-(2-Cyano-6-n-pentanoylamino-phenoxy)-3-tert.butylamino-2-propanol hydrochloride From 11 gm (0.036 mol) of corresponding chlorohydrin and 11.6 ml (0.11 mol) of tert.butylamine, 2.6 gm of hydrochloride were obtained after the addition of HCl. M.p.: 123°–124° C.

EXAMPLE 10

1-[2-Cyano-4-(4-ethylhexanoyl)-amino-phenoxy]-3-tert.butylamino-2-propanol hydrochloride From 15 gm (0.043 mol) of corresponding chlorohydrin and 18 ml (0.17 mol) of tert.butylamine, 4.9 gm of hydrochloride were obtained after the addition of HCl to the amino-alcohol. M.p.: 179°–181° C.

EXAMPLE 11

1-[2-Cyano-4-(2,2-dimethylpropionyl)-amino-phenoxy]-3-tert.butylamino-2-propanol hydrochloride From 10.5 gm (0.032 mol) of corresponding chlorohydrin and 8.7 gm (0.12 mol) of tert.butylamine, 6.8 gm of hydrochloride were obtained after the addition of HCl. M.p.: 225°–228° C.

EXAMPLE 12

1-[2-Cyano-4-(2,2-dimethylpropionyl)-amino-phenoxy]-3-isopropylamino-2-propanol hydrochloride From 10.5 gm (0.032 mol) of corresponding chlorohydrin and 13 ml (0.15 mol) of isopropylamine, 5.7 gm of hydrochloride were obtained after addition to the amino-alcohol. M.p.: 177°–180° C.

EXAMPLE 13

1-(2-Cyano-6-isobutyroylamino-phenoxy)-3-isopropylamino-2-propanol oxalate

From 14.7 gm (0.05 mol) of corresponding chlorohydrin and 8.5 ml (0.1 mol) of isopropylamine, 3.7 gm of oxalate were obtained after the addition of oxalic acid (dissolved in acetonitrile) to the amino-alcohol. M.p.: 196°–198° C.

EXAMPLE 14

1-(2-Cyano-6-isobutyroylamino-phenoxy)-3-tert.-butylamino-2-propanol oxalate From 14.7 gm (0.05 mol) of corresponding chlorohydrin and 10.5 ml (0.1 mol) of tert.butylamine, 4.7 gm of oxalate were obtained after the addition of oxalic acid to the amino-alcohol. M.p.: 232°–234° C.

EXAMPLE 15

1-(2-Cyano-6-n-hexanoylamino-phenoxy)-3-tert.-butylamino-2-propanol oxalate

From 10 gm (0.03 mol) of chlorohydrin, 12.6 ml of tert.butylamine, 5.6 gm of oxalate were obtained after the addition of oxalic acid to the amino-alcohol. M.p.: 143°–144° C.

EXAMPLE 16

1-(2-Cyano-4-n-hexanoylamino-phenoxy)-3-sec.-butylamino-2-propanol

Ten grams (0.035 mol) of 1-(2-cyano-4-n-hexanoylamino-phenoxy)-2,3-epoxypropane were dissolved in 100 ml of ethanol, 7.3 gm (0.1 mol) of sec.-butylamine were added, and the mixture was refluxed for one hour. After the solvent was distilled off in vacuo, the residue was purified by column chromatography in the manner described in Example 6. The base thus obtained was dissolved in ethyl acetate, washed with dilute NaOH and water, dried, and evaporated to dryness. The test substance remaining was recrystallized from ethyl acetate with the addition of petroleum ether. Subsequent recrystallization from acetonitrile yielded 2.4 gm of pure white crystalline base. M.p.: 72°–74° C.

The compounds set forth in Examples 17 to 19 below were prepared by use of analogous procedures.

EXAMPLE 17

1-(2-Cyano-4-n-octanoylamino-phenoxy)-3-sec.-butylamino-2-propanol

From 10 gm (0.0314 mol) of corresponding epoxide and 7.3 gm (0.1 mol) of sec.butylamine, 3.7 gm of base were obtained. M.p.: 83°–86° C.

EXAMPLE 18

1-[2-Cyano-4-(3,3-dimethylbutyroyl)-amino-phenoxy]-3-sec.butylamino-2-propanol From 14 gm (0.0485 mol) of corresponding epoxide and 11.7 gm (0.16 mol) of sec.butylamine, 6.0 gm of base were obtained.

EXAMPLE 19

1-(2-Cyano-4-n-pentanoylamino-phenoxy)-3-tert.-butylamino-2-propanol

Ten grams of corresponding epoxide and 6 gm of tert.butylamine yielded 5.8 gm of pure amine. M.p.: 108°–109° C.

EXAMPLE 20

1-(2-Cyano-4-isobutyroylamino-phenoxy)-3-isopropylamino-2-propanol

An amount of 7.8 gm (0.03 mol) of 1-(2-cyano-4-isobutylroylamino-phenoxy)-2,3-epoxypropane was dissolved in 100 ml of ethanol and then refluxed with 10 ml of isopropylamine for one hour. After the solvent was distilled off, the residue was acidified with HCl and washed with ether. The aqueous phase was rendered alkaline with NaOH, and the base precipitated was extracted with ethyl acetate. The organic extract was washed with H₂O until neutral, dried over Na₂SO₄, and evaporated to dryness in vacuo. The residue was recrystallized twice using active charcoal. An amount of 3.4 gm of pure white crystalline base was isolated. M.p.: 126°–127° C.

The compounds set forth in Examples 21 to 24 below were prepared by use of analogous procedures.

EXAMPLE 21

1-(2-Cyano-4-isobutyroylamino-phenoxy)-3-n-butylamino-2-propanol

From 7.8 gm (0.03 mol) of corresponding epoxide and 10 ml of n-butylamine, 2.8 gm of base were obtained. M.p.: 103°–104° C.

EXAMPLE 22

1-(2-Cyano-4-isobutyroylamino-phenoxy)-3-sec.-butylamino-2-propanol

From 7.8 gm (0.03 mol) of corresponding epoxide and 10 ml of sec.butylamine, 31 gm of base were obtained. M.p.: 107°–108° C.

EXAMPLE 23

1-(2-Cyano-4-n-octanoylamino-phenoxy)-3-isopropylamino-2-propanol

Ten grams (0.0314 mol) of corresponding epoxide were reacted with 6.5 gm (0.11 mol) of isopropylamine, and 4.0 gm of pure base were isolated. M.p.: 116°–118° C.

EXAMPLE 24

1-(2-Cyano-4-isobutyroylamino-phenoxy)-3-tert.-butylamino-2-propanol

By reaction of 10 gm of corresponding epoxide with 10 ml of tert.butylamine, 3.7 gm of pure base were obtained. M.p.: 118°–121° C.

EXAMPLE 25

1-[2-Cyano-4-(2-ethylbutyroyl)-amino-phenoxy]-3-tert.-butylamino-2-propanol hydrochloride Fourteen grams (0.0485 mol) of 1-[2-cyano-4-(2-ethylbutyroyl)-aminophenoxy]-2,3-epoxypropane were dissolved in 100 ml of ethanol, and, after the addition of 14.6 gm (0.2 mol) of tert.butylamine, the mixture was refluxed for one hour. Then, the solvent was distilled off in vacuo, and the residue was acidified with HCl and extracted with ether. The aqueous phase was filtered over charcoal and made alkaline with NH4OH. The base, precipitated as an oil, was taken up in ethyl acetate, washed with water, and dried over MgSO4. After filtration and distilling off of the solvent, the residue was recrystallized from a small amount of acetonitrile. The pure white crystalline base was dissolved in acetonitrile, alcoholic HCl was added, and the crystals precipitated were recovered by suction filtration. The product was recrystallized once more from ethanol, with the addition of ether. An amount of 4.8 gm of pure substance was obtained. M.p.: 214°–217° C.

The compounds set forth in the Examples 26 to 31 below were prepared by use of procedures analogous to that of Example 25.

EXAMPLE 26

1-[2-Cyano-4-(2-ethylbutyroyl)-amino-phenoxy]-3-sec.-butylamino-2-propanol hydrochloride By reaction of 14 gm (0.0485 mol) of corresponding epoxide with 11.7 gm (0.16 mol) of sec.butylamine and addition of HCl, 4.9 gm of hydrochloride were obtained. M.p.: 185°–188° C.

EXAMPLE 27

1-[2-Cyano-4-(2-ethylbutyroyl)-amino-phenoxy]-3-isopropylamino-2-propanol hydrochloride From 14 gm (0.0485 mol) of corresponding epoxide and 11.8 gm (0.2 mol) of isopropylamine, and with the subsequent addition of HCl, 5.2 gm of hydrochloride were obtained. M.p.: 216°–218° C.

EXAMPLE 28

1-[2-Cyano-4-(3,3-dimethylbutyroyl)-amino-phenoxy]-3-isopropylamino-2-propanol hydrochloride By reaction of 14 gm (0.0485 mol) of corresponding epoxide and 11.8 gm (0.2 mol) of isopropylamine, and with subsequent addition of HCl, 6.5 gm of hydrochloride were obtained. M.p.: 135°–137° C.

EXAMPLE 29

1-[2-Cyano-4-(3,3-dimethylbutyroyl)-amino-phenoxy]-3-tert.butylamino-2-propanol hydrochloride By reaction of 14 gm (0.0485 mol) of corresponding epoxide with 11.6 gm (0.16 mol) of tert.butylamine, and with subsequent addition of HCl, 5.3 gm of hydrochloride were obtained. M.p.: 207°–210° C.

EXAMPLE 30

1-(2-Cyano-4-n-butyroylamino-phenoxy)-3-tert.pentylamino-2-propanol hydrochloride From 18 gm of corresponding epoxide and 15 ml. of tert.pentylamine, 7.6 gm of hydrochloride were obtained, after the addition of HCl. M.p.: 144°–146° C.

EXAMPLE 31

1-(2-Cyano-4-acetylamino-phenoxy)-3-isopropylamino-2-propanol hydrochloride

The reaction of 11 gm of epoxide with 10 gm of isopropylamine yielded 3.8 gm of pure hydrochloride, after the addition of HCl. M.p.: 137°–138° C.

The examples below illustrate a few pharmaceutical dosage unit compositions comprising a compound of the present invention as an active ingredient.

EXAMPLE 32

| Tablets | |
|---|---|
| Component | Amount |
| 1-(2-Cyano-4-n-hexanoylamino-phenoxy)-3-tert. butylamino-2-propanol hydrochloride | 40.0 mg |
| Corn starch | 164.0 mg |
| Sec. calcium phosphate | 240.0 mg |
| Magnesium stearate | 1.0 mg |
| | 445.0 mg |

Preparation:

The individual components are admixed thoroughly, and the mixture is granulated in the conventional way. The granulate is compressed into 445 mg tablets, each containing 40 mg of the active ingredient.

EXAMPLE 33

Gelatin capsules

The contents of the capsules are compounded from the following ingredients:

| Component | Amount |
|---|---|
| 1-(2-Cyano-4-n-hexanoylamino-phenoxy)-3-tert. butylamino-2-propanol hydrochloride | 25.0 mg |
| Corn starch | 175.0 mg |
| | 200.0 mg |

Preparation:

The ingredients are admixed thoroughly, and 200 mg portions of the mixture are filled into gelatin capsules of suitable size. Each capsule contains 25 mg of the active substance.

EXAMPLE 34

Injection solution

The solution is compounded from the following ingredients:

| Component | Amount |
|---|---|
| 1-(2-Cyano-4-acetylamino-phenoxy)-3-tert. butylamino-2-propanol | 2.5 parts |
| Sodium salt of EDTA (ethylenediaminetetraacetic acid) | 0.2 parts |
| Distilled water q.s. ad | 100.0 parts |

Preparation:

The active ingredient and the EDTA salt are dissolved in sufficient water, and the solution is diluted with water to the desired volume. The solution is filtered to remove any suspended particles and is filled into 1 cc ampules under aseptic conditions. Finally, the ampules are sterilized and sealed. Each ampule contains 25 mg of the active ingredient.

EXAMPLE 35

| Coated sustained release tablets Core: | |
|---|---|
| Component | Amount |
| (-)-1-(2-Cyano-4-n-hexanoylamino-phenoxy)-3- | 25.0 gm |

-continued

Coated sustained release tablets
Core:

| Component | Amount |
|---|---|
| tert. butylamino-2-propanol hydrochloride | |
| Carboxymethylcellulose (CMC) | 295.0 gm |
| Stearic acid | 20.0 gm |
| Cellulose acetate phthalate (CAP) | 40.0 gm |
| | 380.0 gm |

Preparation:

The active ingredient, the CMC, and the stearic acid are thoroughly admixed, and the mixture is granulated in the conventional way, using a solution of the CAP in 200 ml of a mixture of ethanol and ethyl acetate. Then the granulate is compressed into 380 mg cores, which are subsequently coated in the conventional way with a sugar-containing 5% solution of polyvinylpyrrolidone in water. Each coated tablet contains 25 mg of the active ingredient.

EXAMPLE 36

| Component | Tablets Amount |
|---|---|
| 1-(2-Cyano-4-n-hexanoylamino-phenoxy)-3-isopropylamino-2-propanol | 35.0 gm |
| 2,6-Bis-(diethanolamino)-4,8-dipiperidino-pyrimido-[5,4-d]-pyrimidine | 75.0 gm |
| Lactose | 164.0 gm |
| Corn starch | 194.0 gm |
| Colloidal silicic acid | 14.0 gm |
| Polyvinylpyrrolidone | 6.0 gm |
| Magnesium stearate | 2.0 gm |
| Soluble starch | 10.0 gm |
| Total | 500.0 gm |

Preparation:

The active ingredient is granulated as usual together with lactose, corn starch, colloidal silicic acid, and polyvinylpyrrolidone, after thorough admixture of same by use of an aqueous solution of the soluble starch. The granulate is admixed with the magnesium stearate and compressed to form one thousand 500 mg tablets, each of which contains 35 mg of the first active ingredient and 75 mg of the second active ingredient.

Any one of the other compounds embraced by Formula I or a non-toxic, pharmacologically acceptable acid addition salt thereof may be substituted for the particular active ingredient in Examples 32 through 36. For example, in Example 32, the active ingredient could have been 1-(2-cyano-6-isobutyroylamino-phenoxy)-3-isopropylamino-2-propanol oxalate or 1-(2-cyano-6-n-hexanoylamino-phenoxy)-3-tert.butylamino-2-propanol oxalate in the same amount, and instead of the β-adrenolytically active substance mentioned in Example 36, it is also possible to use the same amount of 1-(2-cyano-6-isobutyroylamino-phenoxy)-3-isopropylamino-2-propanol oxalate. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to those skilled in the art that the invention is not limited to these particular embodiments, and that various changes and modifications may be made without departing from the spirit of the invention or the scope of the appended claims.

We claim:

1. A compound of the formula

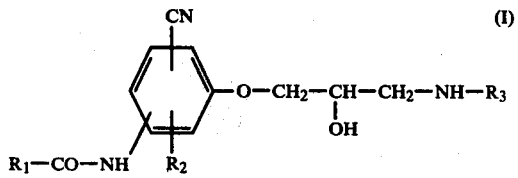

wherein
$R_1$ represents a linear or branched alkyl of from 1 to 20 carbon atoms;
$R_2$ represents a hydrogen or halogen atom, a linear or branched alkyl or alkoxy of from 1 to 4 carbon atoms, or a divalent group —CH=CH—CH=CH— or —(CH$_2$)$_n$—, in which n is an integer of from 3 to 5, with the free valences bonded in the o-position relative to one another; and
$R_3$ represents a linear or branched alkyl of from 3 to 10 carbon atoms, with the provisos that $R_3$ is not tert.butyl when $R_1$ is ethyl or propyl and $R_2$ is a hydrogen atom and that $R_3$ is not isopropyl when $R_1$ is propyl and $R_2$ is hydrogen, or a non-toxic, pharmacologically acceptable acid addition salt thereof.

2. A compound of claim 1, wherein
$R_1$ represents a linear or branched alkyl of from 1 to 7 carbon atoms;
$R_2$ represents a hydrogen atom; and
$R_3$ represents an alkyl branched in the α- or β-position, with the provisos that $R_3$ is not tert.butyl when $R_1$ is ethyl or propyl and that $R_3$ is not isopropyl when $R_1$ is propyl, or a non-toxic, pharmacologically acceptable acid addition salt thereof.

3. A compound of claim 2, wherein $R_1$ is selected from the group consisting of methyl, n-propyl, isopropyl, 1-ethylpropyl, n-butyl, tert.butyl, n-pentyl, neopentyl, 1-ethylpentyl, 3-ethylpentyl, and n-heptyl, and $R_3$ is selected from the group consisting of isopropyl, tert.butyl, sec.butyl, and tert.pentyl, or a non-toxic, pharmacologically acceptable acid addition salt thereof.

4. A compound of claim 2, wherein $R_1$ is n-pentyl and $R_3$ is isopropyl or tert.butyl, or a non-toxic, pharmacologically acceptable acid addition salt thereof.

5. The compound of claim 1 which is 1-(2-cyano-4-n-hexanoylamino-phenoxy)-3-tert.butylamino-2-propanol or a non-toxic, pharmacologically acceptable acid addition salt thereof.

6. The compound of claim 1 which is 1-(2-cyano-4-n-hexanoylamino-phenoxy)-3-isopropylamino-2-propanol or a non-toxic, pharmacologically acceptable acid addition salt thereof.

7. A β-adrenolytic pharmaceutical dosage unit composition consisting essentially of an inert pharmaceutical carrier and an effective β-adrenolytic amount of a compound of claim 1.

8. A method for the treatment or prophylaxis of diseases of the coronaries, for the treatment of hypertension, or for the treatment of cardiac arrhythmia, which comprise administering to a warm-blooded animal or human an effective amount of a compound of claim 1.

9. The method of claim 8 for the treatment of tachycardia.

* * * * *

UNITED STATES PATENT AND TRADEMARK OFFICE
CERTIFICATE OF CORRECTION

PATENT NO. : 4,438,143
DATED : March 20, 1984
INVENTOR(S) : HERBERT KOPPE et al.

It is certified that error appears in the above—identified patent and that said Letters Patent is hereby corrected as shown below:

Column 3, line 26, the moiety "caphor" should read
-- camphor --.

Signed and Sealed this

First Day of January 1985

[SEAL]

Attest:

GERALD J. MOSSINGHOFF

Attesting Officer

Commissioner of Patents and Trademarks